United States Patent [19]

Guirguis

[11] Patent Number: 4,960,130

[45] Date of Patent: Oct. 2, 1990

[54] MODULAR FLUID SAMPLE PREPARATION ASSEMBLY

[75] Inventor: Raouf A. Guirguis, Gaithersburg, Md.

[73] Assignee: Cancer Diagnostics, Inc., Rockville, Md.

[21] Appl. No.: 435,805

[22] Filed: Nov. 14, 1989

Related U.S. Application Data

[62] Division of Ser. No. 308,763, Jan. 10, 1989.

[51] Int. Cl.$^5$ .................................................. A61B 5/00
[52] U.S. Cl. ..................................... 128/760; 604/317; 128/771
[58] Field of Search ....................... 128/760, 761, 771; 604/317, 318, 403, 404; 422/102

[56] References Cited

U.S. PATENT DOCUMENTS

| | | | |
|---|---|---|---|
| 3,777,739 | 12/1973 | Raitto | 128/2 |
| 3,881,465 | 5/1975 | Raitto | 128/2 |
| 4,040,791 | 8/1977 | Kuntz | 23/259 |
| 4,042,337 | 8/1977 | Griffith | 23/259 |
| 4,084,937 | 4/1978 | Beach | 23/259 |
| 4,244,920 | 1/1981 | Manschot et al. | 422/102 |
| 4,473,530 | 9/1984 | Villa-Real | 422/58 |
| 4,492,258 | 1/1985 | Lichtenstein et al. | 141/1 |
| 4,557,274 | 12/1985 | Cawood | 128/760 |
| 4,573,983 | 3/1986 | Annis | 604/322 |
| 4,700,714 | 10/1987 | Fuisz | 128/767 |
| 4,741,346 | 5/1988 | Wong et al. | 128/760 |

Primary Examiner—Max Hindenburg
Attorney, Agent, or Firm—Gipple & Hale

[57] ABSTRACT

An apparatus for collecting biological fluids and handling the same into a sample for testing comprising a tubular container having open ends, one of which is removably secured to a collection storage unit. A shuttle assembly constructed of a cylindrical hollow piston defining a chamber, a top cover covering one end of said piston and a second cover with an aperture and a connector covering the second end of the piston is slidably mounted in the tubular container. An "O" ring is mounted on the exterior surface of the piston to form a fluid tight seal between the "O" ring and the interior surface of the tubular container with the connector being removably secured to a resin/sample container so that movement of the piston in the tubular container carries the resin/sample container into the collection storage unit and forces fluid collected in the tubular container to flow through the resin/sample container.

12 Claims, 7 Drawing Sheets

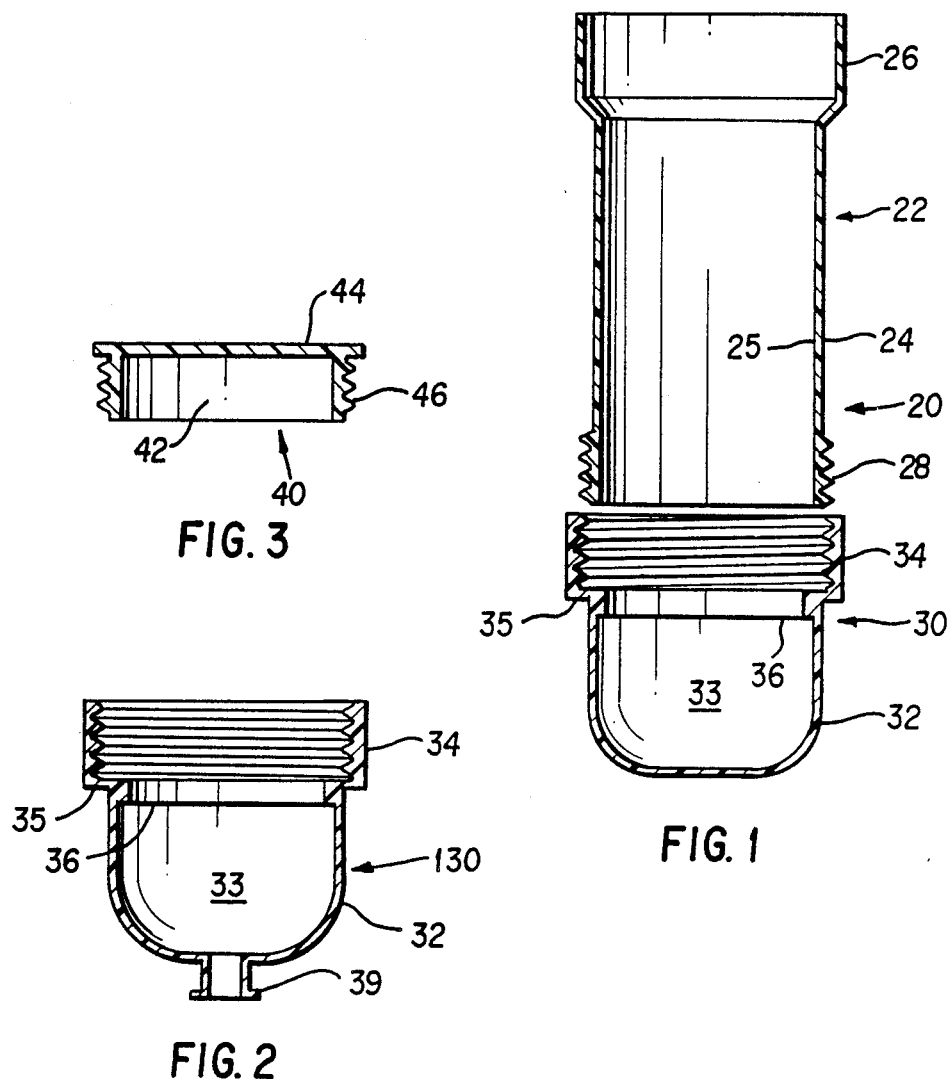

MODULAR FLUID SAMPLE PREPARATION ASSEMBLY

This is a division, of application Ser. No. 07/308,763 filed Jan. 10, 1989, pending.

BACKGROUND OF THE INVENTION

The present invention is directed to medical and laboratory specimen collecting and testing equipment, and more specifically to an apparatus for collecting biological fluids for use in testing.

It is generally necessary in diagnosing and testing for many diseases to collect biological fluids from a patient, e.g., sputum, blood, pleural and peritoneal cavity fluids, urine, etc. for analysis. It is important during the collection handling of biological fluid specimens that the potential of specimen contamination and the spread of any infection from the specimen be minimized. In addition there is also the potential for specimen damage during the collection and/or shipment process as well as the potential for destruction of certain components of the specimen because the packaging does not screen particulants in the fluids or collects and holds different fluid components which will negate the test results or result in false data being obtained when the specimen is tested.

It has been noted that one of the problems in collecting biological fluid specimens occurs not only during the collection of the specimens but also in the transport or shipment of the specimens after collection to the laboratory for analysis.

A typical specimen collecting apparatus is shown by U.S. Pat. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial which in connection with the cap and allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

One such specimen collection device shown by U.S. Pat. 4,040,791 discloses a collection receptacle having a nipple upon which is mounted a specimen container which receives a predetermined amount of the specimen in a sealed condition. The specimen container is provided with an integrally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 which is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy to handle apparatus which obtains fluid samples such as urine with a minimum chance for spillage between collection and laboratory as well as a need to separate various components of the urine. In addition particulates contained in the urine have a valuable medical use so that concentrating the same is beneficial. In using the present invention testing can be performed quickly and accurately with minimum time.

For some testing, particularly where antigens are being removed from the body fluids for a variety of tests it is desirable to remove the antigens from the urine fluid and to concentrate the particulants (e.g. cells, cell debris, etc.) so that various test procedures can be run. It is also desirable to do so with minimal exposure of laboratory personnel to the sample subject of testing. Previously this has been accomplished by a series of tests involving a number of different containers and expensive laboratory equipment. Mass testing using such a series of tests is expensive, time consuming, and often unsatisfactory.

BRIEF SUMMARY OF THE INVENTION

There is provided in the practice of the invention according to the presently preferred embodiment, a urine and blood collection, processing (filtration, concentration, and partial purification of antigen(s) subject to testing) and analysis device. This device is in the form of modular components having a transportable sample compartment in the housing, which through the use of modules can be washed or treated with other fluids allowing the sample then to be quickly analyzed or placed at a controlled temperature for further experimentation as soon as it is received in the laboratory or clinic.

In the accompanying drawings, there is shown an illustrative embodiment of the invention from which these and other of objectives, novel features and advantages will be readily apparent.

BRIEF DESCRIPTION OF THE DRAWINGS

FIG. 1 is a cross sectional view of separated units of the sample collection apparatus of the invention;

FIG. 2 is a cross sectional view of an alternate shuttle storage unit of the sample collection apparatus of FIG. 1;

FIG. 3 is a cross sectional view of a cap for the shuttle storage unit of the sample collection apparatus of FIGS. 1 and 2;

DETAILED DESCRIPTION OF THE INVENTION

Figure 4:
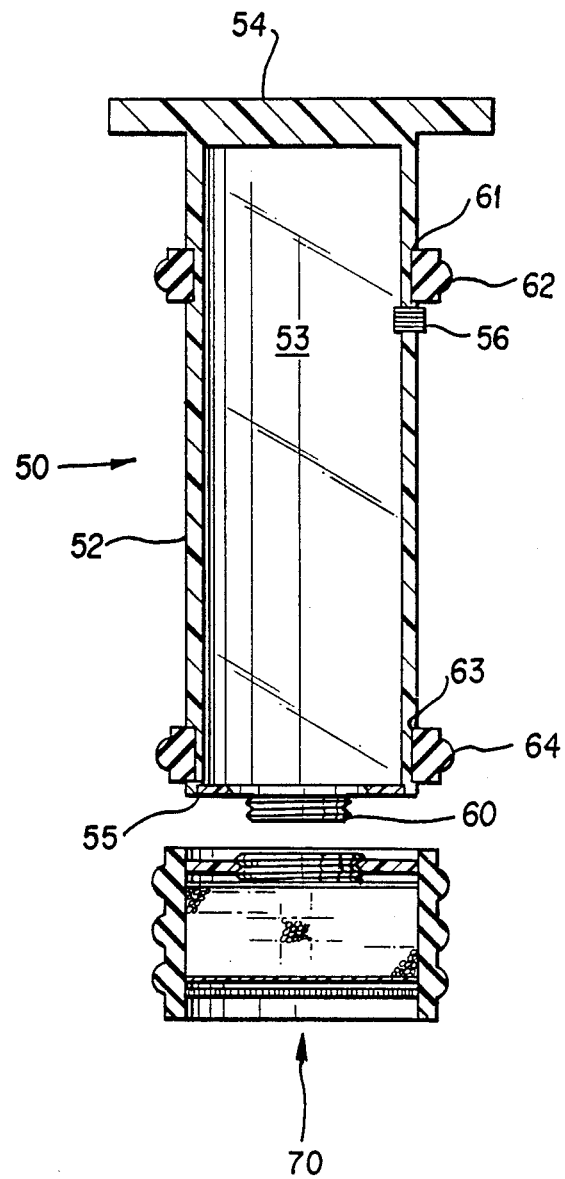
FIG. 4 is an exploded cross sectional view of the piston assembly and resin/sample collection apparatus of apparatus which fits into the sample collection apparatus of FIG. 1.

The preferred embodiment and best mode of the invention is seen in FIGS. 1 and 3 through 8. The invention shown therein comprises a modular fluid resin/-sample containment and sample preparation testing device. While the invention can be used for any body fluid such as sputum, blood, body fluids or urine, it is primarily designed for use in collecting urine/blood samples for use in testing for the presence of various kinds of cancer in the body.

As shown in FIGS. 1 and 3, a sample collection apparatus 20 is constructed of polystyrene and comprises a tubular collection unit 22, a shuttle storage unit 30 and an associated cap member 40. The tubular collection unit 22 is constructed with a tubular open ended cylindrical body 24 having formed on one end an open flared end portion 26 and on the other end threaded portion 28. The flared end portion 26 has a wide mouth to more easily receive body fluid which is loaded into the unit and also prevents entrapment of air between the resin container unit and the surface of the sample fluid. The shuttle storage unit 30 is removably secured to the threaded portion 28. The shuttle storage unit 30 comprises a cylindrical cup shaped body 32 with a stepped female threaded open end 34 and shoulder 35. The open end 34 has a greater diameter than the diameter of body 32. A stop member 36 comprised of a circular ring or integrally formed rib is formed or secured to the inner surface of the shuttle body 32 immediately below the shoulder 35 of the threaded stepped open end 34. This stop member 36 serves as a stop for a transporter or shuttle assembly 50 shown in FIG. 4 which will be discussed later on in the specification. The alternate shuttle storage unit 130 shown in FIG. 2 is like shuttle storage unit 30 except for the needle fitting opening at the bottom of the unit. It is intended for the use of withdrawing blood or other body fluid samples directly from the patient as will be discussed later on in the specification. The cap member 40 as shown in FIG. 3 is formed with a cylindrical body 42 having a lid or cover 44 and external threads 46 which mate with the female threaded end portion 34 of the shuttle body 32. Thus the shuttle storage unit 30 and cap 40 can be used to form a closed container holding the particulants testing material or fluid as desired. It should also be noted that a threaded or snug fitting cap (not shown) can be placed over end position 26 so that the sample collection apparatus can be closed.

The transporter assembly 50 as shown in FIG. 4 is designed to fit within cylindrical body 24 and slideably move along the interior wall surface 25 in a sealed relationship and hold a shuttle resin/sample container 70 for removal or deposit within the shuttle storage body 32. The transporter assembly 50 is constructed of a transparent plastic comprising a hollow cylindrical piston body 52 provided with a thumb cover 54 and a bottom end member 55. An air release aperture 56 is formed in the piston body so that there is communication between the interior chamber 53 of the piston body into the outside atmosphere. A male threaded nipple 60 is formed on the outside of the bottom end member 55 and is provided with a throughgoing aperture (not shown) which communicates with the interior chamber 53. Mounted around the piston body in annular channels 61 and 63 cut into the exterior surface of the body 52 are respectively an upper O-ring 62 and lower O-ring 64. These O-rings slideably engage and form a fluid seal against the interior surface 25 of sample collection unit 22. A shuttle resin/sample container 70 is adapted to be mounted to the nipple 60 and has a diameter or size sufficient to allow it to be seated within the interior 33 of shuttle storage unit 30.

Figure 5:
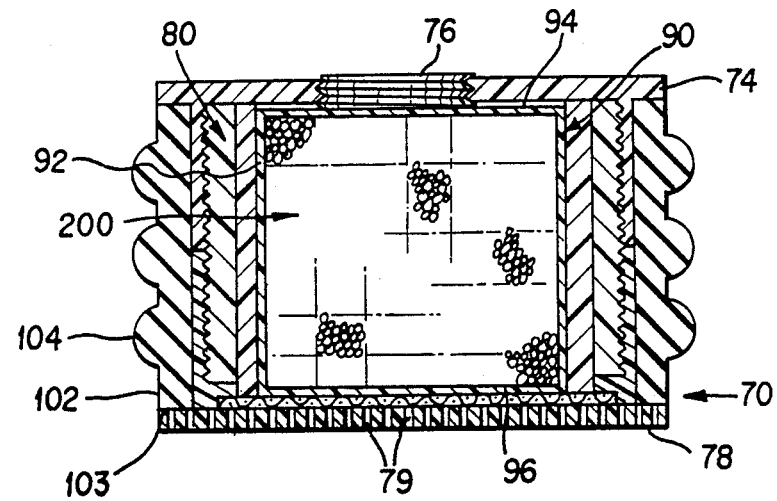
FIG. 5 is an enlarged cross sectional view of the resin/sample container of FIG. 4.
Figure 6:
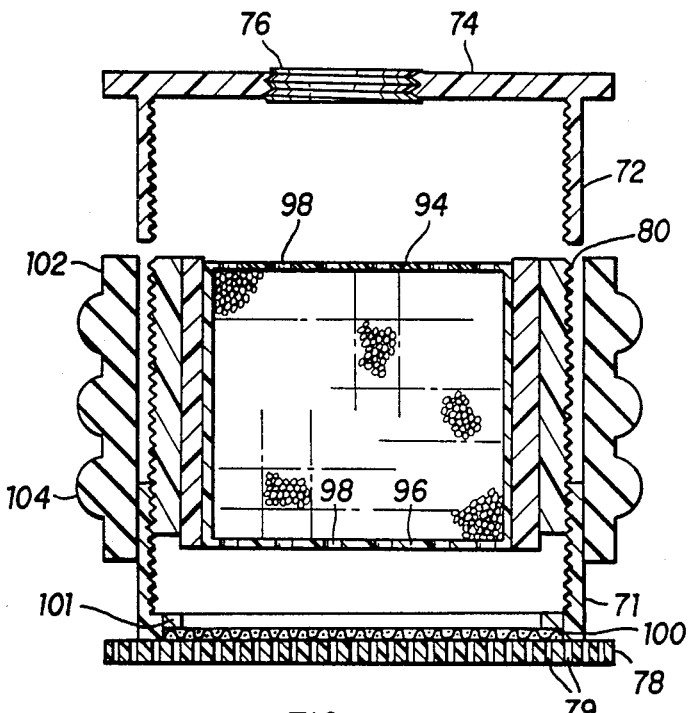
FIG. 6 is an exploded view of the resin/sample container of FIG. 5.

The shuttle sample container 70 as clearly shown in FIGS. 5 and 6 is constructed with a cylindrical body 80 open at both ends and threaded on the outside to allow the mounting of a circular top cover 74 which is threaded on the inside of the cylindrical skirt 72 and provided a throughgoing threaded aperture 76. If desired to improve fluid flow, the top cover 74 can be provided with a plurality of apertures (not shown) which enhance flow through the cover into piston chamber 53. It is of course apparent that the piston bottom end member 55 would also be constructed with complimentary throughgoing apertures. The throughgoing aperture 76 is adapted to receive and mate with the threaded male nipple 60 to allow the same to be fastened to transporter assembly 50 or selectively removed from the transporter assembly 50. A circular bottom cover 78 with a plurality of throughgoing apertures 79 threaded on the inside of its cylindrical skirt 71 is threaded onto the other end of body 80. Positioned inside the body 80 is a snug fitted cylindrical resin module 90. The resin module 90 comprises a cylindrical body 92 and end walls 94 and 96. Both end walls 94 and 96 are formed with porous septums 98 to allow easy flow through of the fluids. A filtration membrane 100 preferably between 0.2–0.5 microns in thickness is positioned between the bottom cover 78, a seal ring 101, and the lower porous end wall 96.

If desired a plurality of membranes can be stacked to obtain the desired filtration. An O-ring sleeve 102 comprising a plurality of O-rings 104 is mounted to the exterior surface of the cylinder formed by the skirt sides of both top and lower covers 71, 72 when the same are fully screwed onto the body of the resin module container 80. 103 of the sleeve 102 abut closely against the planar inner surfaces of the top cover 74 and bottom cover 78 as can be seen in FIG. 5. The resin module 90 may be filled with resin/sample 200 consisting of beads of all forms and sizes which can be specifically manufactured for ion exchange (e.g. Mono Q anion exchange, and Mono P cation exchange from Pharmacia), high affinity chromatography or hydrophobicity (e.g. phenylsepharose beads). Preferably the module holds high affinity resin with specific antibodies immobilized onto the solid phase resin (e.g. protein A, . . .etc.) so that antigens in the sample can bind to their specific antibodies while passing through the resin module and become immobilized as well.

Figure 7:
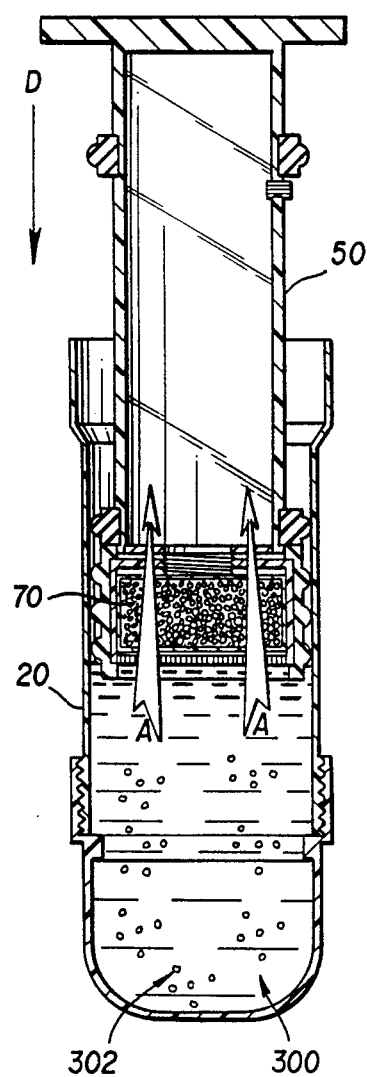
FIG. 7 is a cross sectional view of a sample filtration purification shuttle apparatus with direction of movement of the plunger shown by arrow D' and direction of flow of the fluid shown by arrows A.
Figure 8:
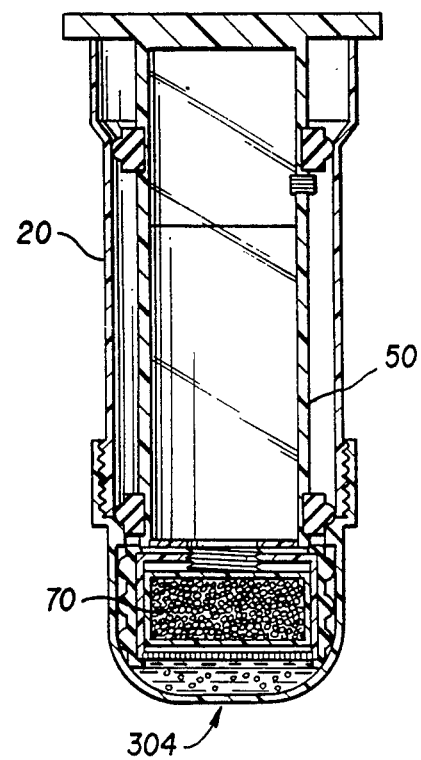
FIG. 8 is a cross sectional view of the filtration purification shuttle apparatus of FIG. 7 with plunger depressed and sample ready for removal.

FIG. 7 shows the sample collection apparatus containing a urine sample 300 having particulate matter 302 therein with a transporter assembly 50 and associated resin/sample container 70 mounted therein. As the shuttle resin/sample container 70 and its associated O-rings 104 is mounted in the interior of the sample collection unit 22, adjacent surface 25, piston 52 is pushed down in the direction shown by arrow D causing the fluid sample 300 to pass through the bottom wall 78, membrane 100 which filters the particulate matter 302, resin module 90 and threaded aperture 76 into the chamber 53. It should be noted that the air contained in chamber 53 is pushed out by the fluid through air release aperture 56 into a chamber formed by the concentric outer surface of the piston body 52 and the inner surface 25 of sample collection unit 22. The shuttle resin/sample container 70 is pushed down until it enters into the body cavity 33 at which time the lower O-ring 64 engages stop rib 36 thus seating the shuttle resin/sample container 70 in a predetermined position so that it cannot break or damage the shuttle storage unit 30. When the shuttle resin/sample container 70 is seated in the shuttle storage unit 30, the upper "O" ring 62 becomes engaged with the inner surface 25 of cylindrical body 24. This will discontinue the communication between the body cavity 53 and the atmosphere through the air release aperture 56. Consequently the fluid entering the body cavity 53 will be trapped inside it even after removal of the shuttle storage unit 30 together with the seated resin/sample container 70. It will also be noted that the particulate matter which has been screened by filteration membrane 100 is thus concentrated at 304 in the bottom of chamber 33 as shown in FIG. 8.

The resin sample material 200 having had flow contact with the fluid 300 captures the specific component of the fluid which is to be tested; in this example, antigens caused by cancer cells. The shuttle storage unit 30 is then unscrewed from the tubular collection unit 22 with the shuttle resin/sample container 70 contained therein, the transporter assembly 50 remaining with the tubular collection unit 22 and cap 40 is screwed on threaded end 34 to keep the sample in a secured contained condition for analysis of the particulate matter or other materials captured by the beads in the resin/sample container.

Figure 9:
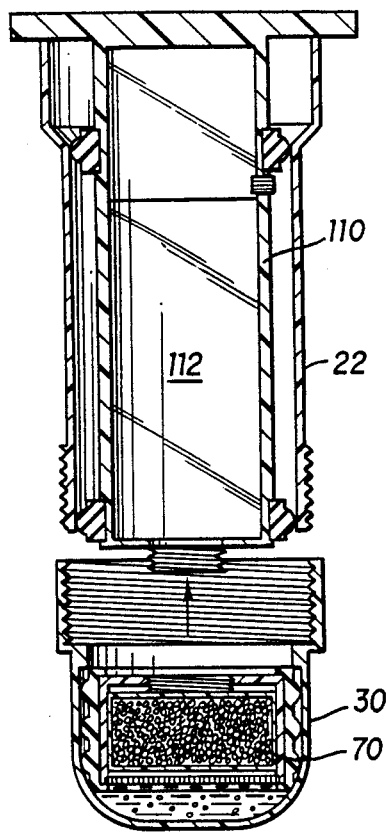
FIG. 9 is a cross sectional view of a filtration purification shuttle with the shuttle storage unit and resin/sample container in a position to be attached.
Figure 10:
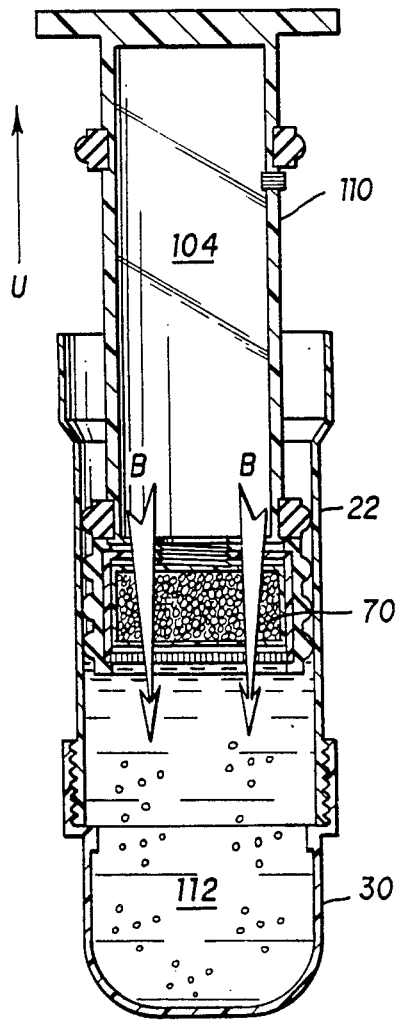
FIG. 10 is a cross sectional view of a filtration purification shuttle connected to a resin/sample container with direction of movement of the plunger shown by arrow U and direction of flow of washing/eluting solution through the resin/sample container shown by arrows B.

If desired the sample or material trapped in the resin/sample container 70 can be washed prior to or after transporting it to the area desired for testing. This washing is shown in FIGS. 9 and 10 in which a prepacked washing/preservative solution module 110 filled with a prepackaged washing and/or preservative solution 112 (e.g. Phosphate buffer saline, tris Hcl buffer, . . . with or without sodium azide as a bacteriostatic agent) is screwed into the aperture 76 of the impregnated resin/sample container 70 by means of a threaded nipple as previously disclosed and placed in a collection apparatus 20 filled with washing solution. The construction of the prepacked washing solution module 100 combines that of the transporter assembly 50 mounted in sample collection apparatus 20. The plunger of the piston is pulled upward in the direction of arrow U as shown in FIG. 10 so that washing solution 112 flows downward through the resin/sample container 70 into chamber 33 of the shuttle storage unit 30. Washing the resin/sample container 70 with the washing buffer solution 112 provides a washed sample.

Figure 12:
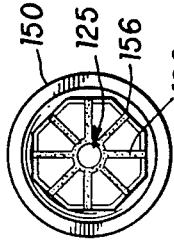
FIG. 12 is a cross sectional view of the bottom surface of the dipstick unit shown in FIG. 11.
Figure 11:
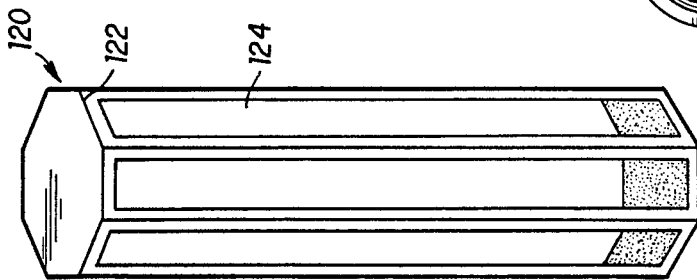
FIG. 11 is an alternate embodiment of the invention showing a removable dipstick unit.

In an alternate embodiment of the invention as shown in FIG. 11 an angular dipstick or testing strip member 120 is provided with a plurality of angular flat sides 122 each of which holds a testing strip 124. The dipstick member 120 is mounted in a testing module 150 which is identical to that previously discussed differing only in that the body fluid as shown in FIG. 7 has been replaced with an elution buffer solution 140 and the dipstick member 120 is to fit tightly positioned in chamber 53 of the piston body. The top cover 154 of the piston can also be provided with an aperture 156 receives a screw cap 158 (not shown) to seat and hold the testing strip member 120 in place. FIG. 12 is a cross sectional view showing the bottom surface of the angular dipstick module 120. A central groove 125 connected to engraved channels 126, directs and distributes the fluid to the dipstick housing. The central groove fits into the nipple hole of the nipple in the dipstick transporter assembly 150. The testing strip member is shown in FIG. 11 and while it is octagonal, it is recognized that it can have any number of sides to hold any number of testing strips to get a plurality of different results such as for example; test strips to test for cancer associated antigens such as transforming growth factors (TGFs), tumor cell motility stimulation factor(s) (AMF), tumor specific markers (e.g. specific prostate cancer marker, aplpha fetoproteins..etc), and test strips to test for proteolytic enzymes associated with tumor invasion and metastases (e.g. collagenases, cathepsins, proteases, . . . etc).

Figure 14:
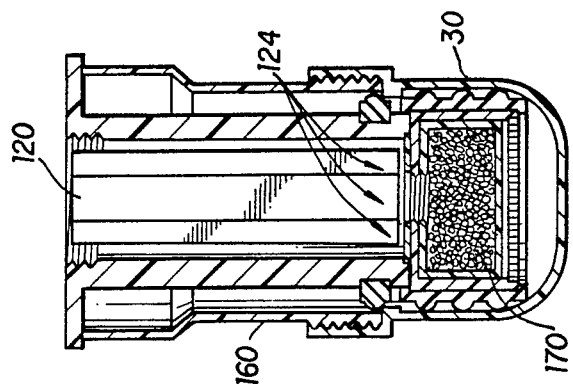
FIG. 14 is a cross sectional view of the apparatus of FIG. 13 showing the dipstick and associated testing strips reacting with concentrated and partially purified antigen.
Figure 13:
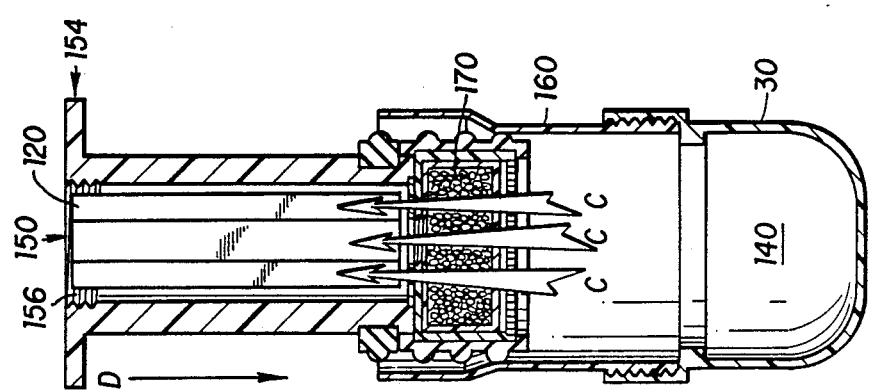
FIG. 13 is a cross sectional view showing movement of the dipstick unit snug fitted into an alternate plunger with direction of movement of the plunger shown by arrow D and direction of flow of eluding concentrate through the resin/sample container shown by arrows C.

In this strip testing procedure the test resin/sample container 170 is screwed into the end of the dipstick transporter assembly 150 in the same manner as previously disclosed and is slid into an eluding buffer unit 160. The removable dipstick unit 120 and associated piston is pushed downward as indicated by arrow D into the eluding buffer solution so that the multiple test strips 124 are soaked with concentrated and partially purified antigen as shown in FIG. 14. The total unit can then be shipped for testing or held for testing the dipsticks or individual testing strips.

Figure 15:
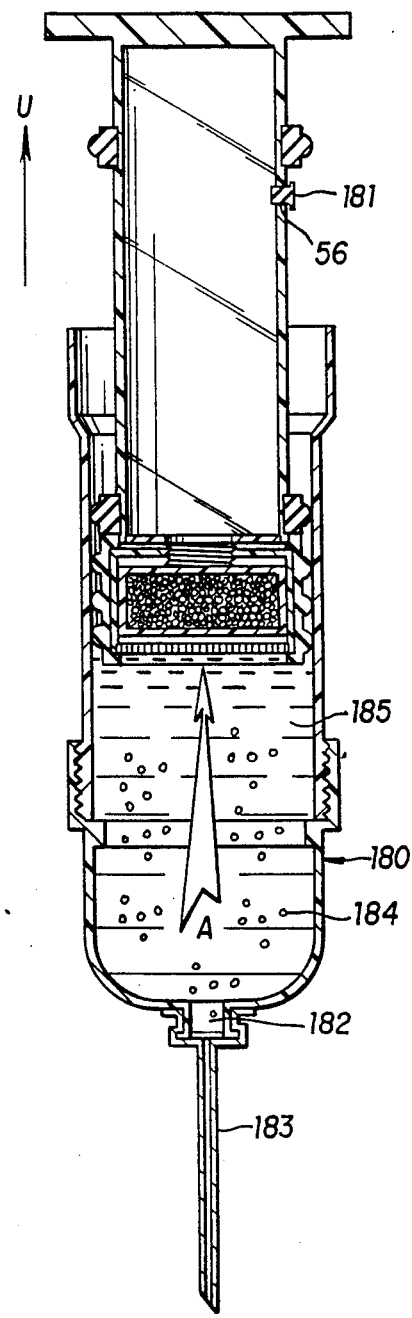
FIG. 15 is an alternate embodiment of the invention showing a sample filtration purification shuttle apparatus with the alternate shuttle storage unit of the sample collection apparatus equipped with a needle and the air release opening closed with direction of movement of the plunger shown by arrow U, and direction of flow of the fluid shown by arrow A.
Figure 16:
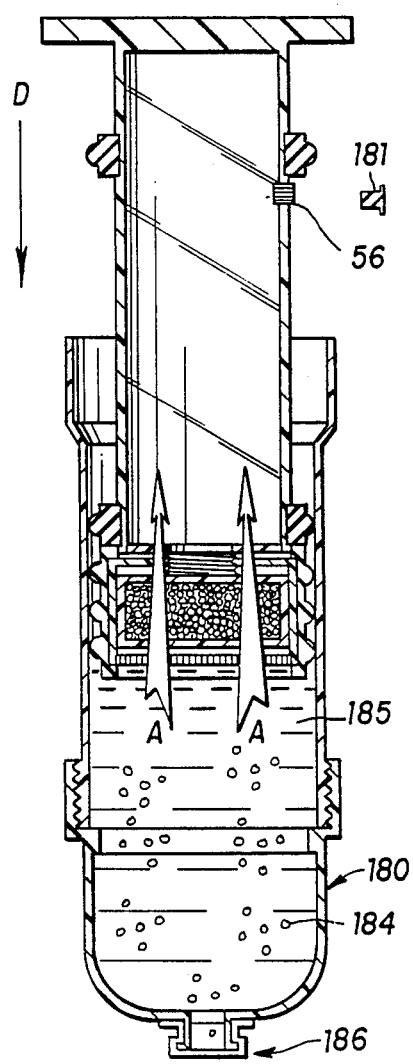
FIG. 16 is a cross sectional view of a sample filtration purification shuttle apparatus of FIG. 15 with the needle replaced with a stopper and the air release plug removed with direction of movement of the plunger shown by arrow D, and direction of flow of the fluid shown by arrows A.

In FIG. 15 an alternate embodiment of the shuttle storage unit is shown where the body of shuttle storage unit 32 is replaced with the alternate body 180 with lure lock opening at the bottom as previously shown in FIG. 2. This permits the use of the device to act as a syringe to withdraw and process blood samples from patients at the same time. As shown in FIG. 15 the air release aperture 56 is blocked with a removable plug 181 during the process of withdrawing blood from the patient and a needle 183 is shown in a locked in position 182. After withdrawing the blood sample the needle is replaced with a lure lock 186 as shown in FIG. 16. The air release plug 181 is then removed and the blood sample 184 and 185 (fluid and particulate matter) will be processed as described earlier in the text.

It can thus be seen that the present invention provides a unique modular usage for collecting, filtering, concentrating, transporting, and purifying the biological fluid sample for use in testing for disease or other analysis.

In the foregoing description, the invention has been described with reference to a particular preferred embodiment, although it is to be understood that specific details shown are merely illustrative, and the invention may be carried out in other ways without departing from the true spirit and scope of the following claims

What is claimed is:

1. An apparatus for collecting biological fluids and holding a predetermined sample for testing comprising a tubular container having open ends; a collection storage unit removably secured to one of said container ends, said collection storage unit having an open end and a closed end, a shuttle assembly slidably mounted in said tubular container, said shuttle assembly comprising a cylindrical hollow piston defining a chamber, a testing means mounted in said piston chamber, a top cover covering one end of said piston and fluid flow means formed on the other end of said piston, said fluid flow means comprising an end member with a connector means mounted therein, said connector means defining a throughgoing bore communicating with said piston chamber, "O" ring means mounted on the exterior surface of said piston to form a fluid tight seal between said "O" ring means and the interior surface of said elongated tubular container, and sample container means removably secured to said connector means and adapted to be seated in said collection storage unit.

2. An apparatus as claimed in claim 1 wherein said testing means comprises a testing body and a plurality of testing strips mounted to said testing body.

3. An apparatus for collecting biological fluids comprising a tubular container having open ends; a collection storage unit removably secured to one end of said container, said collection storage unit having an open end and a closed end, a shuttle assembly slidably mounted in said tubular container, said shuttle assembly comprising a cylindrical hollow piston defining a chamber, testing means mounted in said chamber, said testing means comprising a body and testing strip means mounted to said body, a top cover covering one end of said piston and fluid flow means mounted on the other end of said piston, said fluid flow means comprising an end member with connector means mounted therein, said connector means defining a throughgoing bore communicating with said piston chamber, "O" ring means mounted on the exterior surface of said piston cylinder to form a fluid tight seal between said "O" ring means and the interior surface of said elongated tubular container, and sample container means removably secured to said connector means.

4. An apparatus as claimed in claim 3 wherein said testing strip means comprises test strips to test for cancer associated antigens such as transforming growth factors.

5. An apparatus as claimed in claim 3 wherein said testing strip means comprises test strips to test for tumor cell mobility stimulation factors.

6. An apparatus as claimed in claim 3 wherein said testing strip means comprises test strips to test for tumor specific markers.

7. An apparatus as claimed in claim 6 wherein said tumor specific marker is alpha fetoproteins.

8. An apparatus as claimed in claim 3 wherein said testing strip means comprises test strips to test for proteolytic enzymes associated with tumor invasion and metastatses.

9. An apparatus as claimed in claim 8 wherein said proteolytic enzyme is collagenases.

10. An apparatus as claimed in claim 8 wherein said proteolytic enzyme is cathepsins.

11. An apparatus as claimed in claim 8 wherein said proteolytic enzyme is proteases.

12. An apparatus as claimed om claim 3 wherein said testing strip means comprises a plurality of testing strips, each testing strip indicating a result when contacted by fluid passing through said sample container.

* * * * *